United States Patent
Schaldach

[11] Patent Number: 5,922,015
[45] Date of Patent: Jul. 13, 1999

[54] IMPLANTABLE DEVICE WHICH PERMITS REMOVAL WITHOUT TRAUMATIZING THE SURROUNDING TISSUE

[75] Inventor: Max Schaldach, Erlangen, Germany

[73] Assignee: BIOTRONIK Mess- und Therapiegeraete GmbH & Co. Ingenieurbuero Berlin, Berlin, Germany

[21] Appl. No.: 08/818,395

[22] Filed: Mar. 14, 1997

[30] Foreign Application Priority Data

Mar. 14, 1996 [DE] Germany ............... 196 11 777

[51] Int. Cl.⁶ ........................................ A61N 1/05
[52] U.S. Cl. ............................................. 607/126
[58] Field of Search ................ 607/116, 129–132, 607/126–128, 119–123; 600/372–375, 376–377, 386

[56] References Cited

U.S. PATENT DOCUMENTS

| | | | |
|---|---|---|---|
| 4,258,724 | 3/1981 | Balat et al. | 607/128 |
| 4,341,226 | 7/1982 | Peters . | |
| 4,444,207 | 4/1984 | Robicsek . | |
| 4,628,944 | 12/1986 | MacGregor et al. | 607/126 |
| 5,241,957 | 9/1993 | Camps et al. . | |
| 5,385,579 | 1/1995 | Helland . | |
| 5,658,327 | 8/1997 | Altman et al. | 607/127 |
| 5,716,391 | 2/1998 | Grandjean | 607/126 |

FOREIGN PATENT DOCUMENTS

| | | |
|---|---|---|
| 0589633 | 3/1994 | European Pat. Off. . |
| 0596625 | 5/1994 | European Pat. Off. . |
| 0657185 | 6/1995 | European Pat. Off. . |
| 0668087 | 8/1995 | European Pat. Off. . |
| 4402058 | 4/1995 | Germany . |

OTHER PUBLICATIONS

Saechtling: "Kunststoff Taschenbuch" [Handbook on Plastic]; 23rd Ed., Carl Hanser Verlag München Wien, pp. 330, 331.

*Primary Examiner*—William E. Kamm
*Assistant Examiner*—Kennedy J. Schaetzle
*Attorney, Agent, or Firm*—Venable; George H. Spencer; Catherine M. Voorhees

[57] ABSTRACT

An implantable device for at least temporary electrical contact with body tissue includes a stimulation electrode, a lead having a proximal end connected to a medical device and a distal end securely attached to the stimulation electrode and blocking means for holding the stimulation electrode in its position of contacting the body tissue, counter to a pulling force exerted by the lead. The blocking means is essentially rigid and is at least partially composed of a material that can be resorbed into body fluid. The blocking means includes a holder with a hole which is slipped or fitted onto a surgical thread thereby connecting the blocking means to the surgical thread.

13 Claims, 7 Drawing Sheets

IMPLANTABLE DEVICE WHICH PERMITS REMOVAL WITHOUT TRAUMATIZING THE SURROUNDING TISSUE

BACKGROUND OF THE INVENTION

The invention concerns an implantable device providing temporary electrical contact with body tissue which is preferably the human heart muscle.

For a temporary fastening of a stimulation lead to the heart muscle tissue, the stimulation lead is positioned either on the outside wall of an auricle chamber of the heart with the aid of a holder that is sewn to the auricle wall, or for the stimulation via one of the ventricles, it is inserted into the ventricle tissue with the aid of a surgical thread, the proximal end of which is attached to the stimulation electrode.

A blocking means is provided to prevent the temporarily implanted stimulation electrode from changing the position intended for it during normal axial stressing of the stimulation lead, caused by cardiac action. This blocking means consists either of a holder, which is essentially adapted in shape to the stimulation electrode and is sewn from the outside to the relatively thin auricle chamber wall, or the blocking means is formed by a specially designed segment in the proximal region of the surgical thread, which considerably increases at this point the frictional resistance of the surgical thread relative to the tissue to be stimulated.

If the temporarily implanted stimulation electrode must again be removed from the contacted tissue after a certain period of time, then the effect of the respective blocking means is neutralized by a jolt-type increase in the pulling stress of the stimulation lead that carries the electrode. The lead is relatively easy to move counter to the insertion direction, and the stimulation electrode can be removed.

The solutions known from Prior Art for securing the position of a temporary stimulation electrode, however, have the disadvantage that the contacting tissue is traumatized considerably when the stimulation lead is removed, which leads to severe physical stress for the patient and delays the healing process to an unjustifiable degree.

SUMMARY OF THE INVENTION

Starting with the shortcomings in the Prior Art, it is the object of the invention to develop an electrical contacting device of the aforementioned type, the design of which permits a removal of a temporarily implanted stimulation electrode during a predeterminable time period following the implantation essentially without traumatizing the tissue surrounding the stimulation lead.

The solution is achieved, according to the invention, with an implantable device having a lead with a proximal end connected to a medical device and a distal end securely attached to a stimulation electrode and essentially rigid blocking means for holding the stimulation electrode in its position of contacting the body tissue counter to a pulling force exerted by the lead wherein the essentially rigid blocking means is at least partially made of a material that can be resorbed into body fluid.

The invention includes the realization that the traumatization of the tissue in the region of the stimulation electrode is essentially caused by the fact that the blocking means for the respective stimulation electrode is designed such that a movement of the stimulation electrode is countered by an increased mechanical resistance in order to meet the retaining function. This occurs either through a positive interlocking between stimulation electrode and a holder that must be sewn to the tissue to be stimulated, or by increasing the friction or the resistance of the surgical thread during its movement relative to the tissue to be stimulated.

The blocking means ensures a sufficient fixation of the stimulation electrode and has a relatively large functinal surface. As a result of the large functional surface the blocking means enters into a more or less tight contact with the surrounding tissue during the implantation period. When removing the temporarily implanted electrode, this contact is broken forcibly, leading to the undesired traumatization of the tissue.

As compared to a flexible element, a rigid blocking element has a better retaining effect, which is canceled out again after a time through the resorption of the material into the body fluid, so that the retaining effect is canceled completely. The controllable difference between holding effect and release, which thus appears, is at a maximum.

In accordance with the invention, the blocking means is composed at least in part of a material that can be resorbed into the body fluid, so that a temporarily positioned stimulation electrode can be removed from the body after a period of time with considerably reduced traumatization of the tissue since the effect of the blocking means that blocks an undesired movement is essentially canceled by the volume loss due to resorption.

The blocking means represent a rigid element and is designed such that it can be connected, in particular retroactively, with the surgical thread or the stimulation electrode.

Particular advantages can be achieved for the effect of the blocking means if the shape of the blocking means is changed by means of additional elastic fastening means (in particular means that cannot be resorbed), in dependence on the movement direction of the stimulation electrode, such that they obstruct the movement if the stimulation electrode must be moved counter to its insertion direction during the positioning on the tissue to be stimulated.

In accordance with one preferred embodiment of the invention, the blocking means has a holder, designed such that the stimulation electrode can be secured from the outside on the tissue to be stimulated. The holder has an essentially cup-shaped design and consequently encircles the stimulation electrode partially and form-locking, wherein the surface sections of the stimulation electrode not enclosed by the holder are pressed against the tissue to be stimulated. In order to guide through the connecting lead for the stimulation electrode and a surgical thread used for positioning the electrode, the holder has recesses in the edge region, which are adapted in size to the connecting lead and which encircle one half side of the thread, so that the holder rests with its edge completely on the tissue to be stimulated.

If the holder or at least the aforementioned edge regions of the cup-shaped holder are composed of a material that can be resorbed, then the positive locking necessary for fixing the stimulation electrode at a specific tissue point is canceled after a certain, predeterminable time period. As a result of this, the stimulation electrode can be pulled advantageously from the holder, without causing a stronger traumatization of the tissue.

For one favorable modification of the invention, the holder is provided with rounded-off edges. On the one hand this makes it easier to insert the stimulation electrode into the holder that is sewn to the tissue to be stimulated and, on the other hand, this reduces the possibility of a traumatizing of the tissue when removing the stimulation electrode if the biological decomposition of the material that can be resorbed is not completed.

In accordance with another advantageous embodiment of the invention, the blocking means composed of a synthetic material that can be resorbed is provided on the proximal end of the surgical thread used to insert the stimulation electrode into the tissue to be contacted.

In accordance with a favorable modification of the invention, the blocking means is designed as a disk-shaped element that can be fitted on and has a slot that extends radially from the outside to the inside. The slot has a conical shape in the disk region to make it easier to fit the blocking means onto the surgical thread that projects from the tissue to be stimulated. At the same time, the slot edges in the remaining region, in particular in the end region of the slot, are parallel to each other to ensure a tight seat of the blocking means on the surgical thread. The surgical thread diameter has a larger value for this than the distance between the parallel slot edges.

The blocking means, which is designed such that it can be moved along the surgical thread, extends essentially lateral to the thread direction in accordance with the invention. The fitted-on blocking means can be moved along the surgical thread up to the point where is penetrates the tissue surface. There it rests planar on the body tissue, so that a change in the stimulation electrode position is effectively prevented during normal movement of the stimulated tissue.

In accordance with another modification of the invention, the blocking means that can be resorbed is designed as a sleeve that can be fitted onto the monofilament surgical thread, which sleeve has at least one hook-shaped element. The hook-shaped element projects over the sleeve in longitudinal direction and is designed as a strap, which essentially tapers off conically. The individual blocking means are fitted onto the surgical thread in such a way that the straps of the individual sleeves are arranged alternately. The individual straps are attached to the sleeve with their wider end and extend essentially parallel to the thread axis. Such a fastening advantageously ensures that during the insertion of the thread, the straps fit themselves against the thread during the positioning of the stimulation electrode in the tissue to be contacted, thereby causing only a slight friction resistance. If the pulling tension on the surgical thread is relaxed after the stimulation electrode is positioned, it changes from the completely stretched to a slightly curved shape, owing to its material characteristics. This results in a projecting sideways of the individual straps relative to the thread axis. If a pull is exerted on the connecting wire of such a temporarily implanted stimulation electrode in the direction counter to the insertion direction, the individual straps take on the function of a barb and counteract the movement of the pulling force by blocking it.

In accordance with one advantageous modification, the movement obstructing effect of the blocking means occurs particularly rapidly if the straps are attached to the sleeve, such that they are elastically supported with respect to the axis for the surgical thread and can pivot toward the outside.

Following a predeterminable time period, which is determined by the material used, the blocking means that can be resorbed are decomposed enough so that they can no longer maintain their function as barbs. The temporarily implanted stimulation electrode can then be pulled from the tissue counter to its insertion direction without traumatizing the tissue.

While fitting it onto the proximal end of the monofilament surgical thread, the sleeve-shaped blocking means that can be resorbed is secured with static friction, which is produced in the required amount by adjusting the sizes for the thread and the sleeve diameter.

When extending the sleeve, several strap-shaped, conically tapered elements can be arranged on the outer sleeve wall in such a way that they conform to the sleeve wall when the stimulation electrode is inserted into the tissue to be contacted and as barbs block a movement of the stimulation electrode in the opposite direction. It is favorable if the strap-shaped elements are arranged opposite each other, alternating or in pairs, on the wall of the sleeve-shaped blocking means. The effect of the barb is further increased if the straps, which are attached opposite each other in pairs, are displaced in pairs by 90° in each fastening plane. Following the completion of the time period required for resorption, the electrode can be removed without traumatizing the tissue.

According to another modification of the invention, a rod-shaped blocking means is coordinated with the surgical thread, which is connected by winding the thread around it. The rod-shaped blocking means has a cross hole through which the surgical thread is guided before winding it around the blocking means. The winding around occurs such that the axis for the rod-shaped blocking means is positioned essentially perpendicular to the pulling direction during the removal of the stimulation electrode. Following the complete resorption of the rod-shaped blocking means, the distal end of the surgical thread is released and the temporarily implanted stimulation electrode can be removed without traumatizing the contacted tissue.

In accordance with another embodiment of the invention, a surgical thread is provided, which is composed completely of a material that can be resorbed and has a spiral-shaped segment as blocking means in its proximal region. This spiral is stretched during the insertion of the stimulation electrode as a result of the pulling force exerted on the surgical thread. It essentially resumes its original shape once the stimulation electrode is positioned and thus secures the electrode at the intended position. The stimulation electrode can be removed without traumatizing the tissue once the blocking means or the complete surgical thread has been resorbed.

Good results can be achieved when securing the position of a temporarily positioned stimulation electrode with blocking means made from an osteosynthetic material that can be resorbed, e.g. made of polyglycol acid.

In accordance with yet another embodiment of the invention, the surgical thread is composed of a material that is resistant to pull and can be resorbed. The blocking means is produced by shaping the thread. A sufficient inhibiting of the movement is ensured by a spiral-shaped thread segment as blocking means. The blocking means is provided advantageously at the proximal end of the surgical thread, meaning near the point where the thread is connected to the stimulation electrode. Owing to the intrinsic elasticity of the thread material, the blocking means is overstretched when inserting the stimulation electrode and provides a small resistance to the movement. If there is pulling relief on the distal side of the electrode, the blocking means resumes its original spiral form and inhibits a movement counter to the insertion direction for the stimulation electrode.

DESCRIPTION OF THE DRAWINGS

Advantageous modifications of the invention are characterized in the dependent claims or are shown with the aid of the figures in the following, together with the description of the preferred embodiment of the invention in which:

FIG. 6b is a representation of detail E according to FIG. 6a;

DETAILED DESCRIPTION OF THE INVENTION

Figure 1:
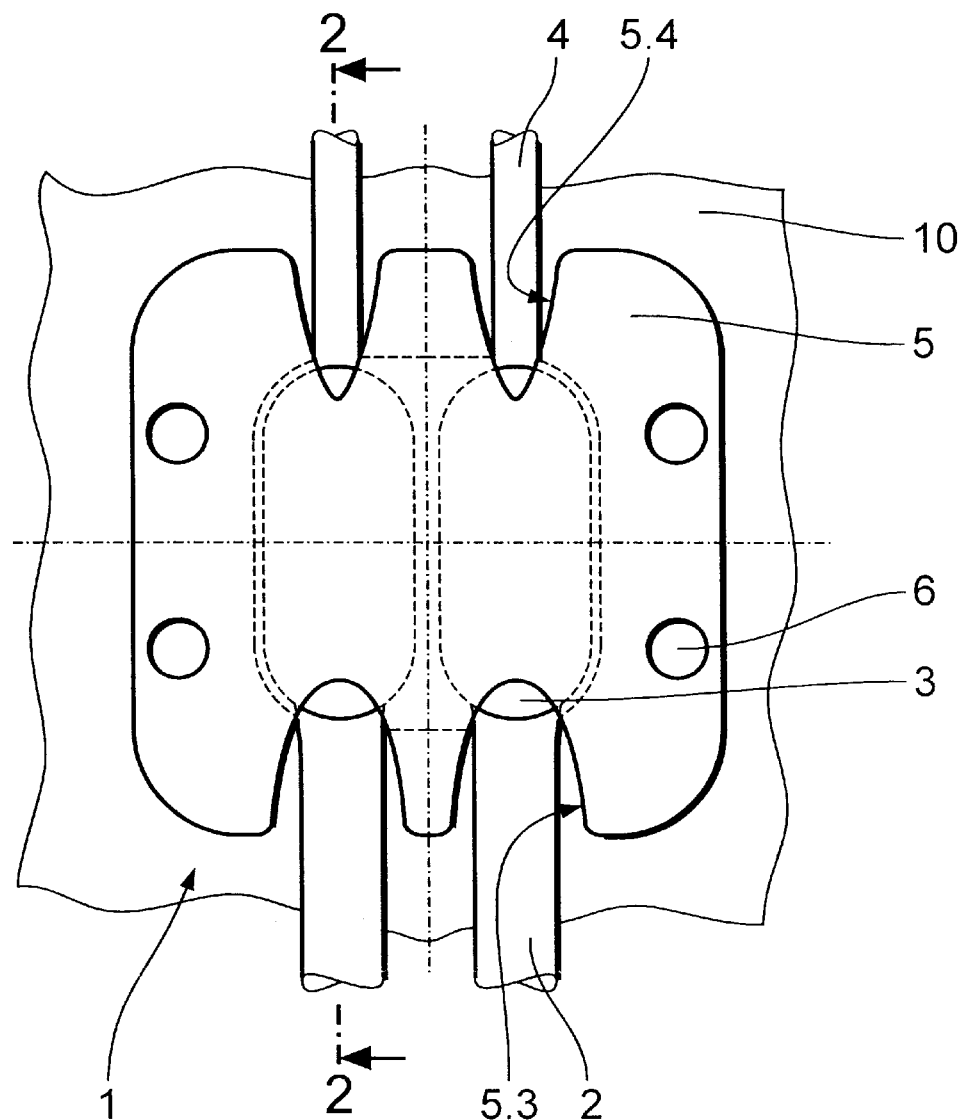
FIG. 1 is a view from above of a tissue segment to be contacted, with a preferred embodiment of the invention.
Figure 2:
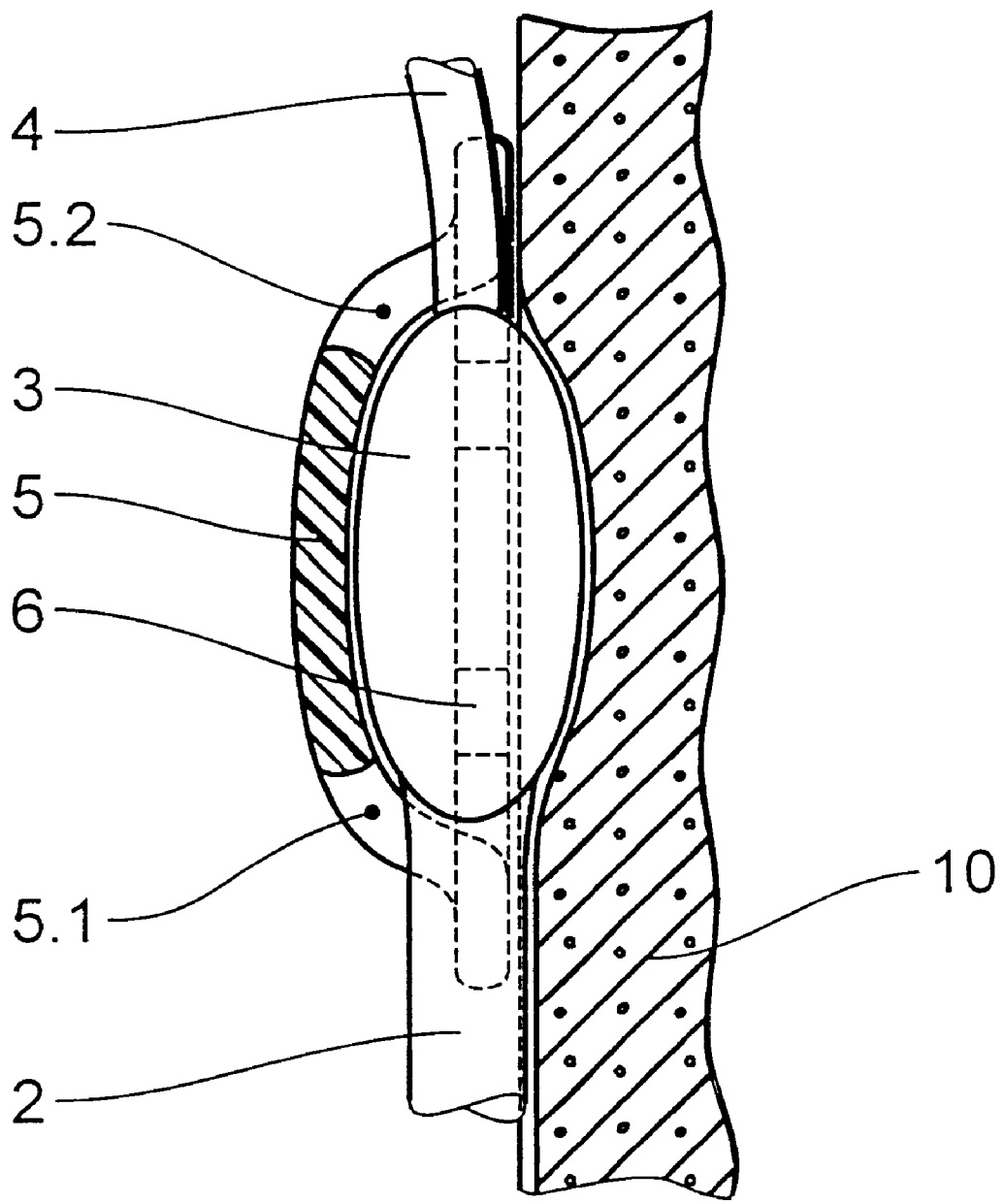
FIG. 2 is a section along the line A . . . A according to FIG. 1.

FIG. 1 shows a view from above of a device 1 with a holder 5, with which two temporarily implanted stimulation electrodes 3 are secured to the tissue of a heart muscle 10 for the purpose of connecting a medical device (not shown). FIG. 2 shows a view of the section along the line A . . . A according to FIG. 1.

The holder 5, which is cup-shaped and is composed of a material that can be resorbed, is fastened to the tissue 10 by using the openings 6 and by sewing it on.

The stimulation leads each have one spherically shaped electrode 3, which is connected on the proximal side with the insulated lead 2 and on the distal side with a surgical thread 4. By utilizing the thread 4, the stimulation electrodes 3 are pulled into the free space between the heart muscle tissue 10 and the holder 5, wherein the holder 5 form-fittingly encircles the electrodes on half the side and pushes them against the flexible heart muscle tissue 10 to make contact. Along its edge, the holder 5 has respectively two identical recesses 5.3 and 5.4 that are limited by the curved shape and are facing each other, which considerably facilitate the insertion of the stimulation electrodes 3 into the free space between tissue 10 and holder 5. It is also of advantage for an easy insertion if all edges of the holder 5 are designed to be rounded.

The stimulation electrodes 3 positioned in this way—in particular in the region for the recesses 5.3 and 5.4—are secured against a sliding out by the edge segments 5.1 and 5.2 of the holder 5, if a pulling force is exerted in axial direction on the electrode 3 or the stimulation lead 2, which force is generated, for example, by the working movement of heart muscle 10.

Since the holder 5 or at least the edge of the holder is composed of a material that can be resorbed, the axial retaining effect of the edge relative to the stimulation electrode 3 is reduced constantly owing to the advancing material decomposition over time, in particular in the region for recesses 5.2 at the edge of holder 5, so that at the completion of a predeterminable time period (selection of material with corresponding decomposition time), the stimulation electrodes can be removed from the holder 5 without resulting in a traumatization of the tissue 10.

Figure 3:
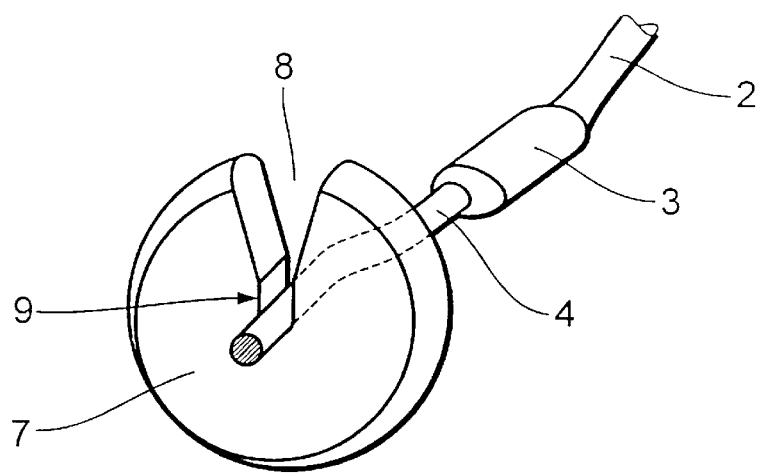
FIG. 3 is another advantageous embodiment of the invention.
Figure 4:
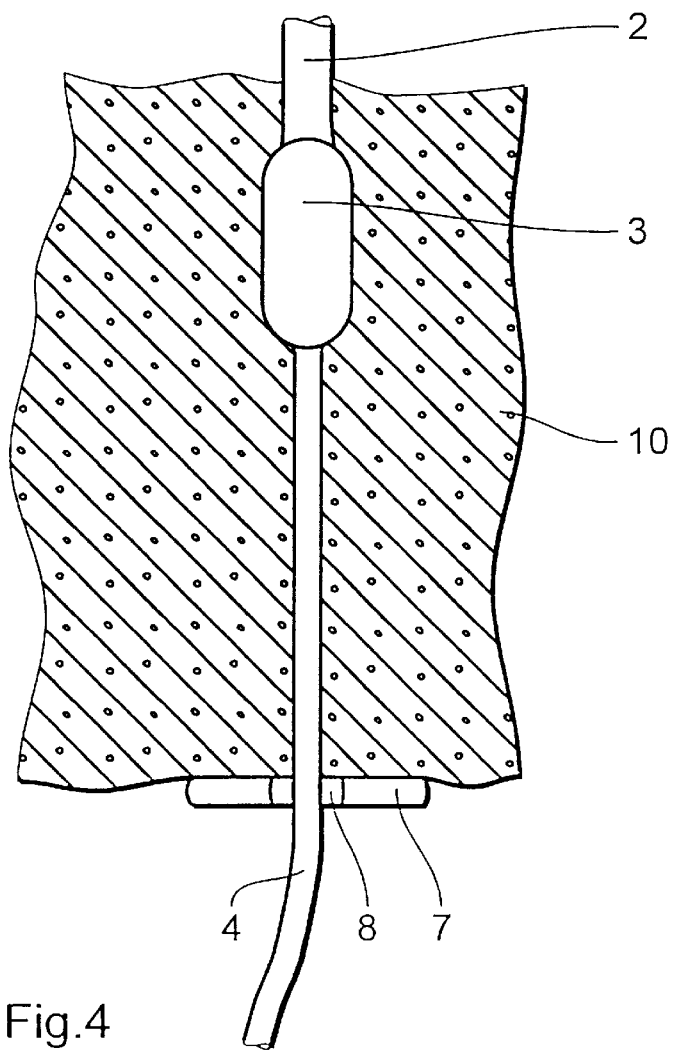
FIG. 4 is a sectional view of a contacted tissue region with an inventive device according to FIG. 3.

The FIGS. 3 and 4 respectively show an embodiment of the invention in a perspective view and in a sectional view through a heart muscle tissue 10 that is contacted by means of a temporary stimulation electrode 3.

A circular disk 7 is provided as blocking means. The disk 7 has a radially extending, peripherally wedge-shaped opened slot 8. With this, the blocking means can easily be fitted onto the distal end of the surgical thread 4 that projects from the heart muscle tissue 10 to be contacted, wherein the blocking means 7 supports itself on the outside of the tissue 10 after being moved along the thread 4. In order to secure a fixed seat on the disk-shaped blocking means 7 on the surgical thread 4, the segment 9 of slot 8 that faces the disk center has parallel edges. The resulting positive locking between thread 4 and blocking means 7 is canceled only if the material that can be resorbed is sufficiently decomposed. Following that, the temporarily implanted stimulation electrode 3 can be removed by applying a pulling stress to the connecting lead 2, without noticeable traumatizing of the heart muscle tissue 10.

The tight seat of the blocking means 7 is achieved with a slot 8, for which the edge distance in the region 9 is smaller than the diameter of the surgical thread 4.

Figure 5:
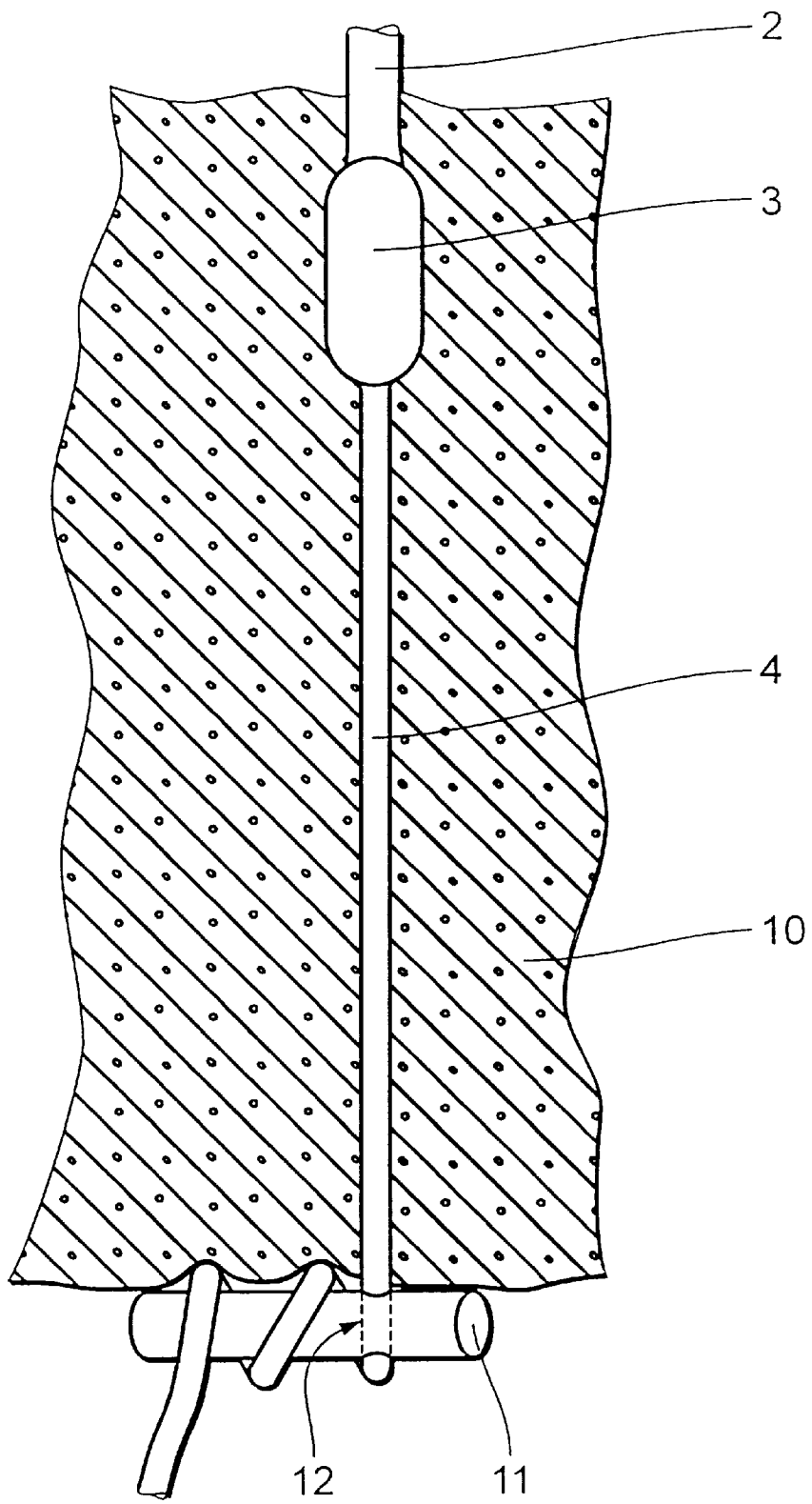
FIG. 5 is a sectional view of a contacted tissue with a favorable modification of the inventive device shown in FIGS. 3 and 4.

The sectional view according to FIG. 5 shows a stimulation electrode 3, temporarily implanted into the heart muscle 10, with connection lead 2, which electrode is placed in the tissue 10 to be stimulated by using a surgical sewing thread 4. A rod-shaped blocking means 11 of a material that can be resorbed is provided to secure the planned position for the stimulation electrode 3. The blocking means 11 has a cross hole 12, through which the distal end of the surgical thread 4 that projects from the tissue 10 is guided. After it is wrapped with the thread end, the rod-shaped blocking means 11 supports itself on the tissue outside, wherein the longitudinal axis of the blocking means 11 extends essentially perpendicular to the axis for the surgical thread 4. Owing to static friction and positive friction, two to three windings of the thread already will result in a sufficiently tight seat for the blocking means 11. Following the decomposition of blocking means 11 that can be resorbed, the surgical thread 4 is released again and the stimulation electrode 3 can be removed without problems by pulling on the connection lead 2.

Figure 6:
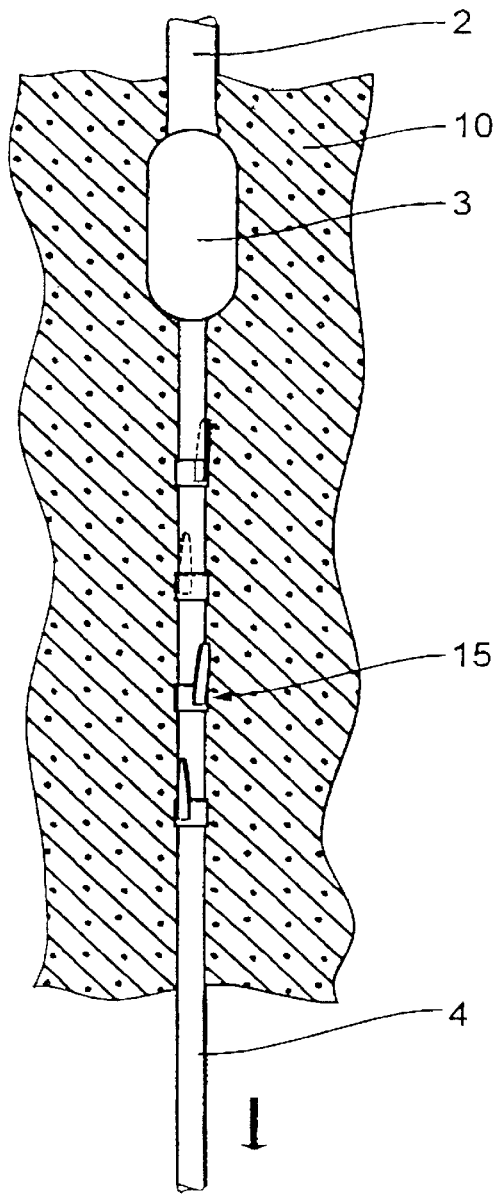
FIG. 6 is a sectional view of a contacted tissue region with another embodiment of the invention during the phase where the stimulation electrode is inserted.
Figure 6A:
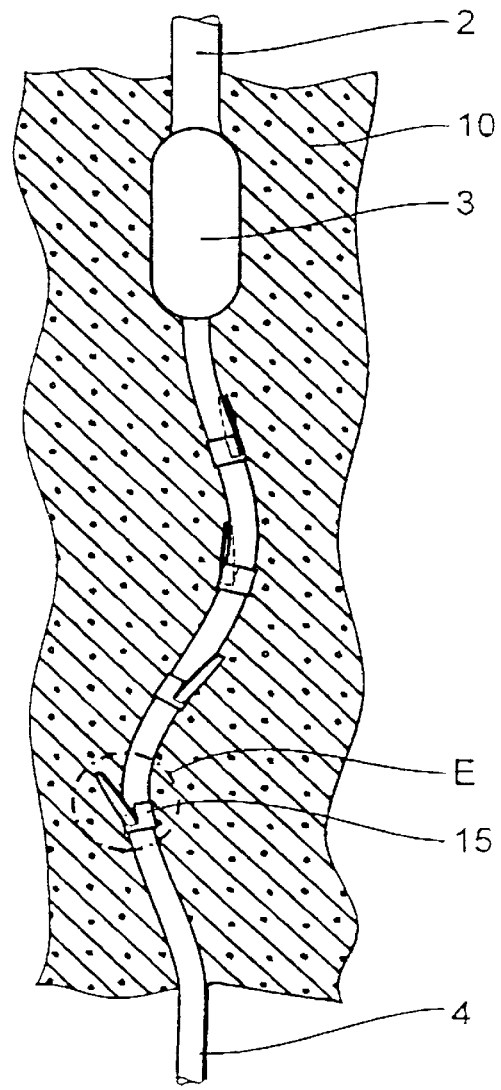
FIG. 6a is a sectional view of the contacted tissue region according to FIG. 6, following implantation of the electrode.
Figure 6B:
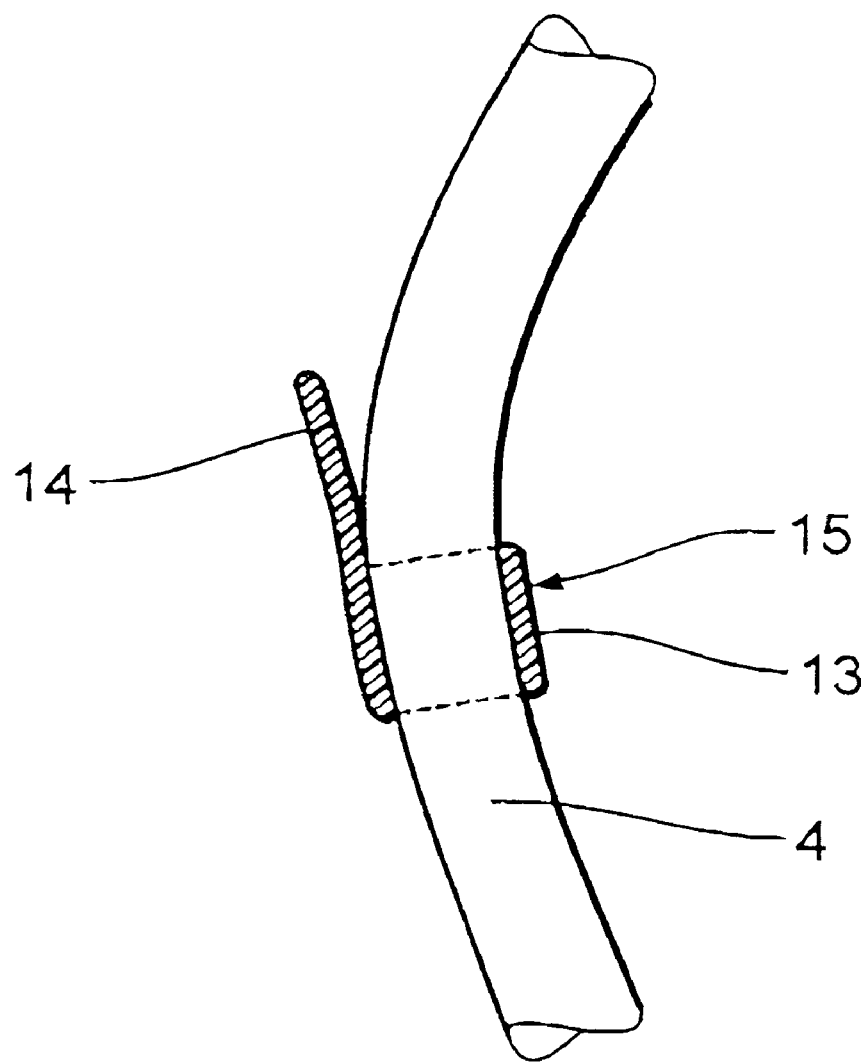

A device with blocking means 15 that can be fitted onto the surgical thread 4 is shown in the FIGS. 6, 6a and 6b. The sleeve-shaped blocking means 15 are arranged at the proximal end of the surgical thread 4 and have a separate holding element 14, which conforms in the direction of the sleeve axis during the insertion of the surgical thread 4 into the tissue 10. The holding element 14 is designed in the shape of a conically tapered strap, which is fastened with the wider end to the sleeve 13 and projects over it lengthwise (compare FIG. 6b).

The blocking means 15 are arranged in a row on the thread such that their strap-type holding elements 14 are arranged essentially alternating, wherein they extend essentially parallel to the axis of the surgical thread 4. When inserting the stimulation electrode 3 into the heart muscle tissue 10, the surgical thread is pulled in the direction of the arrow (FIG. 6), and the holding elements 14 of blocking means 15 conform to the sleeve or thread axis. As a result of this, only a slight additional frictional resistance is generated by the blocking means 15 during the penetration of the heart muscle tissue. Once the stimulation electrode has been placed, no pulling tension acts upon the surgical thread 4 (FIG. 6a) and, owing to its intrinsic stress, the thread 4 assumes a curved shape inside the tissue 10. As a result of this, the holding elements 14 project out by a certain measure (FIG. 6b). The holding elements 14 then extend essentially tangential to the axis for the surgical thread and thus act as barbs counter to the insertion direction for thread 4. The same effect is achieved if a pulling force is exerted on the electrode lead in the direction counter to the insertion direction of the thread.

The blocking effect of the holding elements 14 is reduced more and more as time goes on by the material decomposition of the material that can be resorbed, so that the stimulation electrode 3 can be removed from the heart muscle tissue 10 without resistance after a preset time period, which is determined by the selection of the material for the blocking means.

Figure 7:
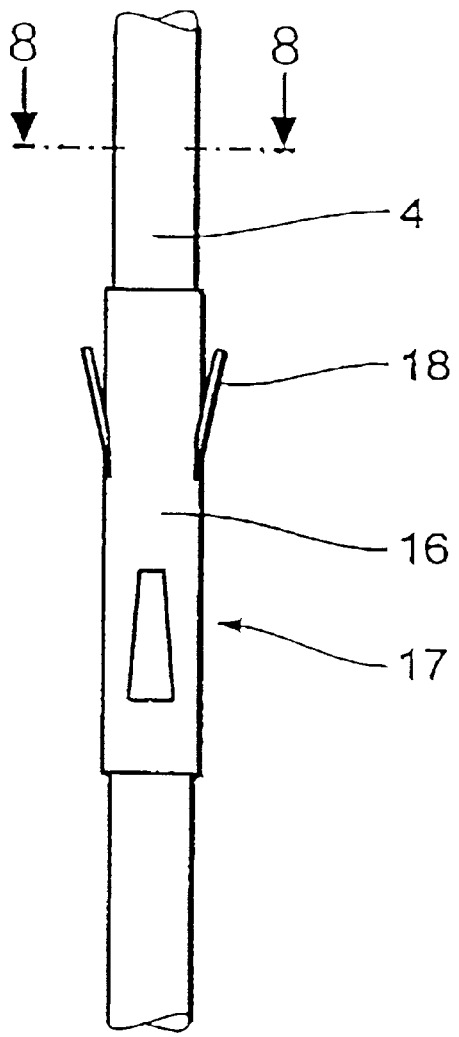
FIG. 7 is a representation of a favorable modification of the invention shown in FIG. 6; as well as FIG. 8 is a representation of a section along the line B . . . B according to FIG. 7.
Figure 8:
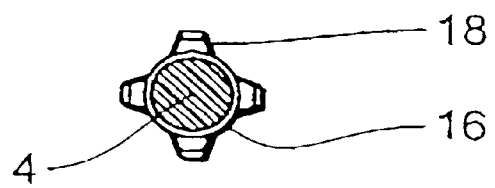

The blocking means 17 that can be resorbed, shown in a view from the side in FIG. 7, is formed as a long sleeve and is fitted onto the proximal region of the surgical thread 4. The holding elements 18 are formed in pairs onto the outside wall of the sleeve 16 in two superimposed planes. The holding elements 18 are designed as small, conically tapered straps and are attached with their wide ends to the sleeve 16. The holding elements 18 are arranged in each plane facing each other, wherein the holding elements of one plane are in a position that is displaced by 90° relative to the holding elements in the other plane. With the sectional view along the line B . . . B, as shown in FIG. 7, FIG. 8 illustrates the arrangement of the individual holding element pairs, for which the axis is positioned at a small, pointed angle to the axis of the surgical thread 4. If the surgical thread is pulled through the heart muscle tissue to be stimulated for the purpose of positioning a temporary stimulation electrode (not shown), then the holding elements 18 conform to the sleeve wall, thereby reducing the frictional resistance of the thread. If the thread 4 is moved in opposite direction, the holding elements 16 project out and function to counter this movement like barbs.

This quality is used for securing a stimulation electrode that is temporarily implanted in a heart muscle tissue, which can be removed without traumatizing the tissue following completion of a preset time period upon which the retaining effect of the barb is canceled through material decomposition.

The slant at which the holding elements 14, 18 shown in FIGS. 6, 6a, 6b, 7 and 8 project out can be increased simply in that the holding means in a flexible positioning arrangement are attached pivoting to the respective sleeve 13, 16 of the blocking means 15, 17.

The invention in its design is not limited to the aforementioned, preferred exemplary embodiment. Rather, a number of variants are conceivable that make use of the presented solution, even with basically different embodiments.

It is obvious that the rigid blocking means that can be resorbed can be provided in a plurality of variants of an implantable electrode and its lead as well as a fastening means connected to the electrode.

I claim:

1. In an implantable device for at least temporary electrical contact with body tissue comprising a stimulation electrode, a lead having a proximal end connected to a medical device and a distal end securely attached to the stimulation electrode and blocking means for holding the stimulation electrode in its position of contact with the body tissue, counter to a pulling force exerted by the lead wherein the improvement comprising the blocking means being essentially rigid and being at least partially composed of a material that can be resorbed into body fluid, said blocking means including a holder with a hole, said holder with a hole being slipped or fitted onto a surgical thread thereby connecting said blocking means to the surgical thread.

2. The improvement according to claim 1, wherein the essentially rigid blocking means is designed such that it is inclined counter to the direction of the pulling force.

3. The improvement according to claim 1, wherein the essentially rigid blocking means can be connected to the stimulation electrode by means of the holder.

4. The improvement according to claim 3, wherein the holder has an essentially cup-shaped design with an edge, and at least some part of the edge is composed of a material that can be reabsorbed.

5. The improvement according to claim 4, wherein recesses are provided in the cup edge, which form a passage and at least partially encircle one of the stimulation electrode and the surgical thread.

6. The improvement according to claim 1, wherein the holder encircles the thread in the form of an essentially form-fitting sleeve.

7. The improvement according to claim 6, wherein said holder is a sleeve and said essentially rigid blocking means further includes a holding element connected elastically to the sleeve so that the blocking means will conform to the surface of the surgical thread when the stimulation electrode is inserted into the tissue, said holding element being a conically tapered strap which outwardly projects from the sleeve in the form of a barb if a counter pulling force is exerted on the surgical thread.

8. The improvement according to claim 1, further comprising a plurality of said blocking means arranged in a row on the surgical thread; and wherein said holder is a sleeve and each blocking means further includes a holding element elastically connected to the sleeve, said holding elements being displaced by 90° with respect to the preceding holding element.

9. The improvement according to claim 1, wherein said holder is a sleeve and said essentially rigid blocking means further includes holding elements connected elastically to the sleeve, said holding elements being arranged in pairs on an outer wall of the sleeve and being displaced in pairs by 90° with respect to the preceding pair of holding elements.

10. The improvement according to claim 1, wherein a polyglycol acid is used as the material that can be resorbed.

11. The improvement according to claim 1, wherein the holder encircles the stimulation electrode in the form of an essentially form-fitting sleeve.

12. The improvement according to claim 1, wherein the blocking means has a disk-shaped design with a radially extending slot that opens outward for guiding a thread through it.

13. The improvement according to claim 1, wherein the holder is a sleeve and said essentially rigid blocking means further includes a holding element connected elastically to the sleeve, the holding element having the shape of a conically tapered strap, which is fastened with the wider end to the sleeve and projects over the sleeve lengthwise.

* * * * *